United States Patent [19]

Vasile

[11] 4,253,337

[45] Mar. 3, 1981

[54] ULTRASONIC NONDESTRUCTIVE TESTING METHOD

[75] Inventor: Carmine F. Vasile, Thousand Oaks, Calif.

[73] Assignee: Rockwell International Corporation, El Segundo, Calif.

[21] Appl. No.: 64,925

[22] Filed: Aug. 8, 1979

[51] Int. Cl.³ .............................................. G01N 29/04
[52] U.S. Cl. ......................................... 73/599; 73/600
[58] Field of Search .................. 73/599, 600, 579, 577, 73/582, 588

[56] References Cited

U.S. PATENT DOCUMENTS

| 3,115,770 | 12/1963 | Cram et al. | 73/600 |
| 3,436,958 | 4/1969 | Proctor | 73/600 |

Primary Examiner—Anthony V. Ciarlante
Attorney, Agent, or Firm—H. Fredrick Hamann; Craig O. Malin; John J. Deinken

[57] ABSTRACT

Disclosed is a method for evaluating a discontinuity in an object. As used to measure the depth of a surface discontinuity in a plate type of object, the method includes the steps of generating a horizontally polarized shear wave in the object directed substantially along the axis of the discontinuity, passing the generated wave through an aperture to diffract the wave prior to its arrival at the discontinuity, detecting the wave after it has propagated through the discontinuity, and calculating the depth of the discontinuity by correlating the phase and amplitude of the detected wave to the phase and amplitude of a similar wave propagated in a region of the object which is free of discontinuities.

9 Claims, 2 Drawing Figures

ULTRASONIC NONDESTRUCTIVE TESTING METHOD

BACKGROUND OF THE INVENTION

This invention is related to nondestructive testing methods and, more particularly, to such methods employing the generation and detection of ultrasonic waves.

An increasing concern with efficiency and economy in many areas of modern structural design has motivated more widespread use of nondestructive testing methods. Nondestructive methods are important because of their ability to locate a structural defect at an early stage in the life of the defect, so that the appropriate corrective action, such as removing and replacing the defective component, can be initiated before such a defect leads to a catastrophic failure of a component. Before such testing methods became available, it was necessary to design structural components with the assumption that flaws of a certain size were present in the building materials. This practice led to the need to provide structural components of sufficient size and strength to function properly even when such defects were present. When nondestructive testing measures can be implemented, however, similar structural components may be manufactured and installed at a lower expense by reducing the size, substituting less expensive materials, etc. Flaws and other defects of a magnitude which might cause failure in these less expensive components can then be detected by nondestructive testing methods and remedied before such undesirable consequences occur. In this manner, nondestructive inspection techniques can be utilized to maintain the desired level of reliability in structural designs while at the same time reducing construction costs.

One type of defect which plays a significant role in the prediction of structural failure is a discontinuity, such as a crack, a weld, or a slot, in a material. A number of methods for evaluating such flaws are known in the nondestructive testing art. Some of the known methods which utilize ultrasonic waves, for example, direct an ultrasonic signal toward the side of the discontinuity. The discontinuity will then reflect and refract the ultrasonic wave energy in a characteristic manner. This characteristic interaction has been measured in prior art techniques be detecting a change in the coefficient of the reflected wave, detecting a change in the transmission coefficient of the transmitted wave, or by observing a mode conversion to another type of ultrasonic wave motion. These changes are typically utilized to estimate such parameters as the depth of the discontinuity, which parameters can then be utilized to predict the remaining useful life of the component before a failure occurs due to the defect.

For defects smaller than a certain size, however, such known ultrasonic methods do not exhibit sufficient sensitivity to provide useful information about the defect. Where a thin, shallow slot is present in a plate type of material, for example, the sensitivity of such methods appears to decrease as the square of the ratio between the depth of the slot and the thickness of the plate. Consequently, a need has developed in the art for an ultrasonic nondestructive evaluation method exhibiting sufficient increased sensitivity to be capable of characterizing small discontinuities in an object.

SUMMARY OF THE INVENTION

It is a general object of this invention to provide a new and improved method for evaluating a discontinuity in an object utilizing ultrasonic waves.

A method of evaluating a discontinuity in an object, according to this invention, includes the steps of:

(a) generating an ultrasonic wave in the object directed substantially along the axis of the discontinuity;

(b) passing the generated wave through an aperture to diffract the wave prior to its arrival at the discontinuity;

(c) detecting the wave after it has propagated through the discontinuity; and (d) characterizing the discontinuity according to the differences between the generated and detected waves.

In a more particular embodiment, step (b) may include calculating the depth of the discontinuity by relating the changes in the phase and amplitude of the detected wave to similar values for a wave propagating in the absence of a discontinuity. The wave generation and detection locations are preferably spaced on the object such that the length of the discontinuity constitutes a substantial proportion of the distance travelled by the wave. The discontinuity may be, for example, a crack, a weld, or a slot in the object.

In a more particular embodiment, a method of measuring the depth of a surface discontinuity in a plate type of object, according to the invention, includes the steps of:

(a) generating a horizontally polarized shear wave in the object directed substantially along the axis of the discontinuity;

(b) passing the generated wave through an aperture to diffract the wave prior to its arrival at the discontinuity;

(c) detecting the wave after it has propagated through the discontinuity; and (d) calculating the depth of the discontinuity by correlating the phase and amplitude of the detected wave to the phase and amplitude of a similar wave propagated in a region of the object which is free of discontinuities.

Examples of the more important features of the invention are broadly outlined in this summary in order to facilitate an understanding of the detailed description that follows and so that the contributions which this invention provides to the art may be better appreciated. There are, of course, additional features of the invention, which will be further described below and which are included within the subject matter of the appended claims.

BRIEF DESCRIPTION OF THE DRAWINGS

Additional objects, features, and advantages of the present invention will become apparent by referring to the detailed description below of the preferred embodiments in connection with the accompanying drawings, wherein like reference numerals refer to like elements throughout all the figures. In the drawings.

DETAILED DESCRIPTION OF THE PREFERRED EMBODIMENT

Figure 1:
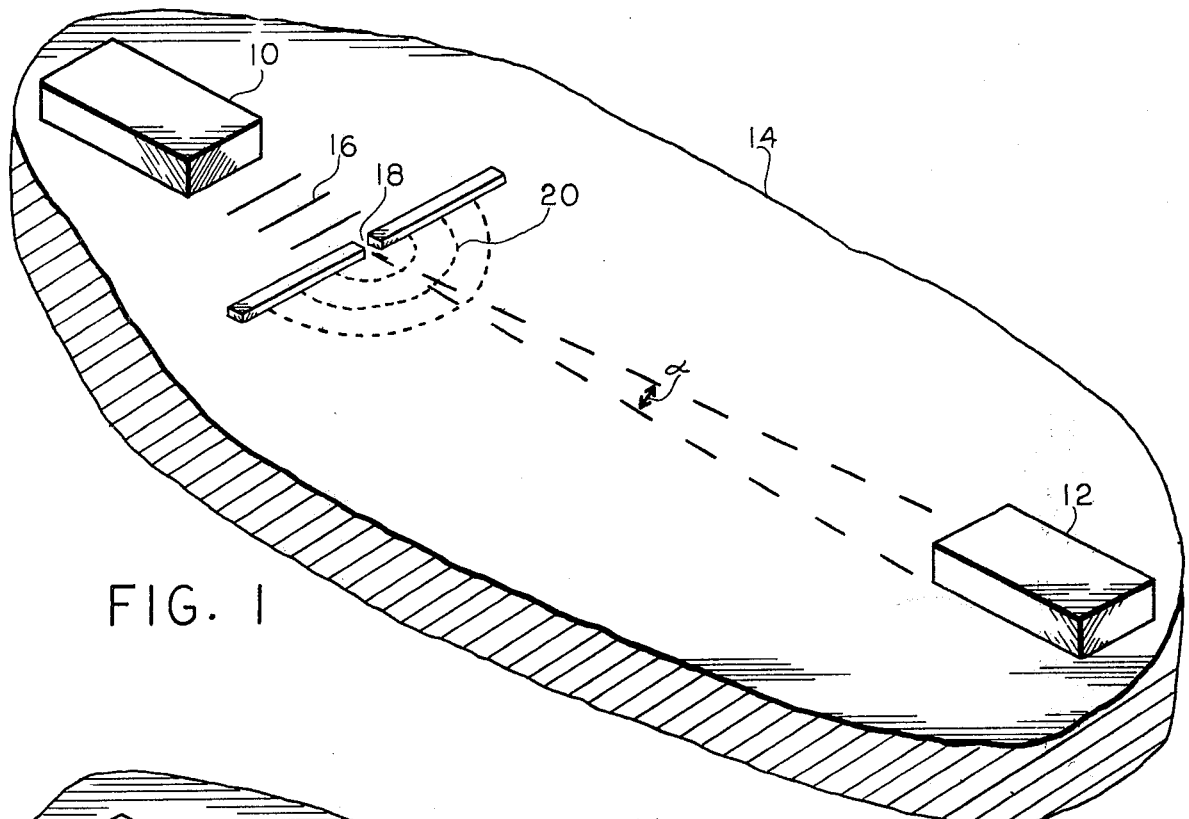
FIG. 1 is a perspective view schematically depicting the operation of the present invention on a plate in an area where no flaws are present.

Now referring to FIG. 1, a perspective view is provided illustrating an apparatus which is configured for practicing the method of this invention. The apparatus includes an ultrasonic transmitting transducer 10 and a receiving transducer 12, which are placed proximate the surface of a plate 14 which is to be tested for the presence and extent of discontinuities in the plate.

A number of different types of transducers suitable for use in this invention are known in the art. The electromagnetic acoustic transducer (EMAT), for example, may be used in practicing the method of this invention. An EMAT will generate or detect ultrasonic waves in an electrically conductive material without the need to establish contact between the material and the transducer, a feature which is advantageous in many testing applications. The periodic permanent magnet EMAT, such as that disclosed in U.S. Pat. No. 4,127,035, may be used to generate horizontally polarized shear (SH) waves in a plate type of material, such as the plate 14.

The circuitry used to drive the transmitting transducer 10, and to receive and analyze signals generated by the receiving transducer 12, is not shown in FIG. 1. The design and use of such circuitry is well known, however, as will be appreciated by those skilled in the art, so that there is no need to illustrate specific examples here.

As is shown somewhat schematically in FIG. 1, the transmitting transducer 10 is used to generate a horizontally polarized shear wave, represented by the lines 16, in the object 14. An aperture 18 is positioned so that the generated wave must pass through the aperture, thereby creating, by diffraction, a circular wavefront in the object, as represented by the semicircular lines 20. Although the aperture 18 is shown in FIG. 1 as a separate structure for purposes of clearly illustrating the method of this invention, it will be appreciated by those skilled in the art that the aperture can be incorporated into the structure of the transducer, so that the transducer itself generates a suitably diffractive wave. For a region of the plate 14 in which the propagation of the diffracted wave is undisturbed by flaws, as is depicted in FIG. 1, the diffracted wave will progress through the object with a uniform divergence, eventually arriving at the receiving transducer 12, where the wave will be detected. The magnitude of the response of the receiving transducer will be proportionate to the amount of wave energy reaching the plate 14 under the transducer, so that the response can be related to the ultrasonic energy contained in the angular segment $\alpha$ of the diffracted wave.

Figure 2:
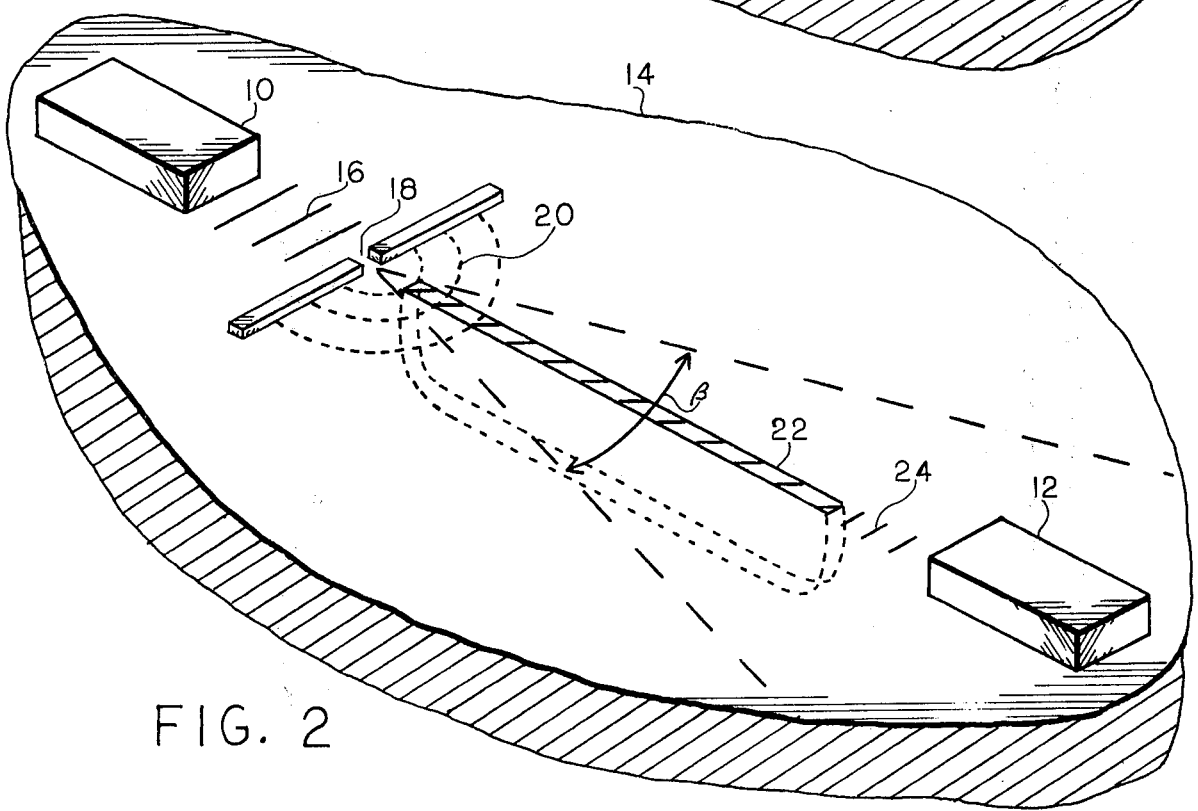
FIG. 2 is a perspective view schematically depicting the operation of the invention in the presence of a flaw on the plate.

It is an outstanding feature of this invention to provide a new technique utilizing ultrasonic waves for evaluating a discontinuity in a material. As shown schematically in FIG. 2, an ultrasonic wave propagation pattern in an object is affected substantially by the presence of a discontinuity. In FIG. 2, the transducers 10 and 12 are placed in the vicinity of a slot 22 in the plate 14. In addition, the transducers are aligned so that the ultrasonic wave generated by the transducer 10 will be directed substantially along the axis of the discontinuity. This alignment is in marked contrast to the usual practice in prior art methods of directing the ultrasonic wave generally toward the side of a crack or other discontinuity. As in FIG. 1, the transmitting transducer 10 generates a horizontally polarized shear wave, represented by the lines 16, which is diffracted by the aperture 18 so that the wavefront becomes circular, as represented by the semi-circular lines 20. Upon reaching the slot 22, however, a portion of the ultrasonic energy in the wavefront corresponding to the width of the slot is channeled into the slot. This portion of the ultrasonic wave then travels through the slot, so that the slot acts, in effect, as a waveguide. As a consequence, both the phase and amplitude of the wave will be affected. At the far end of the slot, the ultrasonic wave energy passes out of the slot, as indicated by the lines 24, and is detected by the receiving transducer 12.

As shown in FIG. 2, the angular segment $\beta$ of the circular ultrasonic wavefront which is guided toward the receiving transducer by the slot 22 can be significantly larger than the corresponding angular portion $\alpha$ arriving at the receiving transducer in the absence of a discontinuity, as depicted in FIG. 1. Thus, the amplitude of the detected wave will be greater due to the waveguiding effect of the slot, and this change in amplitude can be utilized to characterize the slot 22. The angle $\beta$ is inversely proportional to the width of the slot, so that the amplitude difference may be made large by adjusting the placement of the transducers 10 and 12 so that the length of the slot 22 constitutes a substantial proportion of the distance travelled by the wave in the plate. The data obtained by this method might typically be used to calculate the depth of the slot by relating the changes in the phase and the amplitude of the detected wave to similar values for a wave propagating in the absence of a slot. In one test of this method, a 0.5 MHz SH wave was propagated through a 0.3 inch wide aperture and generated in a 0.063 inch thick aluminum plate containing a slot 6 mils wide and through 10% of the thickness of the plate. Such a slot was found to produce a reflection coefficient of only 5%, but an 18% increase in the transmission amplitude was obtained using the slot as the waveguide according to the method of this invention.

In conclusion, although typical embodiments of the present invention have been illustrated and discussed herein, numerous modifications and alternative embodiments of the method of this invention will be apparent to those skilled in the art in view of this description. For example, the invention might be utilized to measure parameters of discontinuities in materials other than depth. Moreover, objects configured in shapes other than a plate might be tested according to this method. Furthermore, the invention may be practiced with types of ultrasonic waves other than horizontally polarized shear waves. Accordingly, this description is to be considered as illustrative only and is provided for the purpose of teaching those skilled in the art the manner of performing the method of this invention. Furthermore, it should be understood that the form of the invention depicted and described herein are to be considered as the presently preferred embodiments. Various changes may be made in the configurations, sizes, and arrangements of the components of the invention, as will be recognized by those skilled in the art, without departing from the scope of the invention. Equivalent elements, for example, might be substituted for those illustrated and described herein, parts or connections might be reversed or otherwise interchanged, and certain features of the invention might be utilized independently of the use of other features, all as will be apparent to one skilled in the art after receiving the benefit attained through reading the above description of the invention.

What is claimed is:

1. A method of evaluating a discontinuity in an object comprising the steps of:
   (a) generating an ultrasonic wave in the object directed substantially along the axis of the discontinuity;
   (b) passing the generated wave through an aperture to diffract the wave prior to its arrival at the discontinuity;
   (c) detecting the wave after it has propagated through the discontinuity; and
   (d) characterizing the discontinuity according to the differences between the generated and detected waves.

2. The method of claim 1, wherein step (d) further comprises:
   (d) calculating the depth of the discontinuity by relating the changes in the phase and amplitude of the detected wave to similar values for a wave propagating in the absence of a discontinuity.

3. The method of claim 1, wherein the generated wave is a horizontally polarized shear wave.

4. The method of claim 3, wherein the object evaluated is a metallic plate.

5. The method of claim 1, wherein the wave generation and detection locations are spaced on the object such that the length of the discontinuity constitutes a substantial proportion of the distance travelled by the wave.

6. The method of claim 1, wherein the discontinuity is a crack in the object.

7. The method of claim 1, wherein the discontinuity is a weld in the object.

8. The method of claim 1, wherein the discontinuity is a slot in the object.

9. A method of measuring the depth of a surface discontinuity in a plate type of object comprising the steps of:
   (a) generating a horizontally polarized shear wave in the object directed substantially along the axis of the discontinuity;
   (b) passing the generated wave through an aperture to diffract the wave prior to its arrival at the discontinuity;
   (c) detecting the wave after it has propagated through the discontinuity; and
   (d) calculating the depth of the discontinuity by correlating the phase and amplitude of the detected wave to the phase and amplitude of a similar wave propagated in a region of the object which is free of discontinuities.

* * * * *